United States Patent [19]

Grainger

[11] 4,198,391
[45] Apr. 15, 1980

[54] PHARMACEUTICAL COMPOSITIONS

[75] Inventor: Norman Grainger, London, England

[73] Assignee: R. P. Scherer Ltd., Slough Berks, England

[21] Appl. No.: 834,887

[22] Filed: Sep. 20, 1977

Related U.S. Application Data

[63] Continuation of Ser. No. 596,406, Jul. 16, 1975, abandoned, which is a continuation-in-part of Ser. No. 488,695, Jul. 15, 1974, abandoned.

[30] Foreign Application Priority Data

Jul. 20, 1973 [GB] United Kingdom ............... 34804/73

[51] Int. Cl.² ...................... A61K 9/48; A61K 31/705
[52] U.S. Cl. ......................................... 424/37; 424/182
[58] Field of Search .................................. 424/37, 182

[56] References Cited

U.S. PATENT DOCUMENTS

| | | | |
|---|---|---|---|
| 2,052,150 | 8/1936 | Torigian | 424/182 |
| 2,298,122 | 10/1942 | Hailer et al. | 424/37 |
| 2,415,312 | 2/1947 | Thompson et al. | 424/182 |
| 2,698,822 | 1/1955 | Halpern et al. | 424/182 |
| 2,765,256 | 10/1956 | Beals et al. | 424/182 |
| 2,780,355 | 2/1957 | Palermo et al. | 206/84 |
| 2,860,086 | 11/1958 | Stoll et al. | 424/182 |
| 2,870,062 | 1/1959 | Stanley et al. | 424/37 |
| 3,139,383 | 6/1964 | Neville | 424/37 |
| 3,418,999 | 12/1968 | Davis | 424/14 |
| 3,536,074 | 10/1970 | Aufhauser | 128/222 |
| 3,784,684 | 1/1974 | Bassert et al. | 424/37 |
| 3,867,521 | 2/1975 | Miskel et al. | 424/37 |
| 4,088,750 | 5/1978 | Cresswell | 424/37 |

FOREIGN PATENT DOCUMENTS

7/44488 7/1974 South Africa .
754489 8/1956 United Kingdom .
784201 10/1957 United Kingdom .
788698 1/1958 United Kingdom .

OTHER PUBLICATIONS (1971) Hagers, "Pharmazgutischen Praxis," Springer/-Verlag, Berlin, Ger., Kapseln, pp. 482–491.
(1971) Boehringer, "Lanitop" B-methyl-digoxin, Nov. 1971, Dec. 1971, Kapseln, 12 pp., Misc. Adv. and Mfg. Prod. Inform.
(1972) Martindale Extra Pharmacopeia, 26th Ed., Pharm. Press, London, pp. 622–630, Digitalis Cardiac Elycosides.
(1973) British Pharmaceutical Codex. Pharm. Press., London, pp. 162–163 "Digitoxin-Digoxin".
Hom et al., J. Pharm. Sci. 59(6): 827–830, Jun. 1970 "Oral Dosage Form Design and its Influence on Dissolution Rates for a Series of Drugs".
Huffman et al., J.A.M.A. 222(8): 957–960, Nov. 20, 1972, "Absorption of Orally Given Digoxin Preparations.
Lindenbaum Pharmacol. Rev. 25(2): 229–237, Jun. 1973 "Bioavailability of Digoxin Tablets".
R. P. Scherer Corp. Annual Report (1974) 2 pp., (1973) 2 pp., (1972) 2 pp.

*Primary Examiner*—Shep K. Rose
*Attorney, Agent, or Firm*—Allegretti, Newitt, Witcoff & McAndrews

[57] ABSTRACT

A cardiotonic dosage unit form comprises a soft gelatin capsule containing a liquid cardiotonic composition comprising (a) a cardiac glycoside, preferably digitoxin or digoxin; (b) ethanol; (c) water; (d) propylene glycol and/or glycerine; and (e) a liquid polyethylene glycol; the cardiac glycoside preferably being present in an amount of from 50 to 300 micrograms.

4 Claims, No Drawings

PHARMACEUTICAL COMPOSITIONS

REFERENCE TO RELATED APPLICATION

This is a continuation application of application Ser. No. 596,406, filed July 16, 1975, which is a continuation-in-part application of application Ser. No. 488,695, filed July 15, 1974, both now abandoned.

BACKGROUND OF THE INVENTION

Field of the Invention and Description of the Prior Art

This invention is concerned with improvements in and relating to pharmaceutical compositions and, more particularly, relates to cardiotonic compositions containing as active ingredient, a cardiac glycoside derived from *Digitalis purpurea* or *Digitalis lanata* or a derivative thereof. For convenience, such materials will hereinafter be simply referred to as "cardiac glycosides".

Cardiac glycosides are widely used cardiotonic agents and are commonly formulated as tablets for oral administration. Of necessity, each tablet must contain a very small amount of the active ingredient, (e.g. 250 micrograms or less) since these particular active agents are administered in such very small doses, almost always less than 0.5 mg. The fact that each tablet has to contain so little of the active ingredient gives rise to problems in formulation and, in particular, makes it very difficult to insure perfect compounding of the tableting mix so that each tablet contains the same amount, within tolerable limits of the active ingredient (see for example, Thomas et al, The Lancet, Dec. 1, 1973, pp. 1267-8; Fraser et al, 5, Pharm. Pharmac., 1973, 25, pp 268-973; and Shaw et al, British Medical Journal, 1973, 4, pp 763-766).

SUMMARY OF THE INVENTION

It is an object of the present invention to provide an improved dosage unit suitable for the oral administration of a cardiac glycoside.

Further purposes and objects of the present invention will appear as the specification proceeds.

Accordingly, the present invention provides a cardiotonic dosage unit form comprising a soft gelatin capsule containing a liquid cardiotonic composition comprising
(a) a cardiac glycoside; (b) ethanol; (c) water; (d) propylene glycol and/or glycerin, and (e) a liquid polyethylene glycol.

DETAILED DESCRIPTION OF THE PREFERRED EMBODIMENT

The cardiac glycoside used in the compositions of the invention may be, for example, digoxin, digitoxin, digitalin, lanatoside C, acetyl digitoxin, acetyl digoxin or methyl digoxin. The most generally preferred cardiac glycosides are digitoxin and digoxin, especially the latter.

The compositions in accordance with the invention will generally be prepared by dissolving the cardiac glycoside in a mixture of the ethanol and water and for this purpose it is generally preferred that the amount of water be as small as possible, but sufficient to insure solution of the active ingredient in the water/alcohol mixture and will most generally be present in an amount by weight less than the amount by weight of ethanol, the water, preferably forming less than 25% by weight of the total water/ethanol mixture. Suitably, the weight ratio of water/ethanol mixture of cardiac glycoside is of the order of about 80:1 or even higher.

The solution of cardiac glycoside is mixed with the propylene glycol (glycerin) polyethylene glycol mixture and the polyethylene glycol forms the major component of the compositions of the invention generally being present in the amounts of at least 75% by weight, preferably from 80-95% by weight, of the total composition contained in the soft gelatin capsule.

The gelatin capsule will be one formed of gelatin containing a plasticiser such as glycerin, propylene glycol, diethylene glycol or hexanetriol. Further, the plasticiser may comprise one of those mentioned above together with sorbitol in order to improve the properties of the capsules with respect to exposure to moisture containing atmospheres. The amount of sorbitol will preferably be about equal to the amount of glycerin or other plasticiser. Accordingly, a preferred capsule contains gelatin plasticised with from about 8 to 15% of weight of glycerin preferably about 12.5% by weight, and from 12.5 to 15% by weight of sorbitol, preferably about 13.5% of sorbitol, the percentages being based on the total weight of gelatin, glycerin and sorbitol.

The total weight of ingredients contained in the gelatin capsule of the compositions of the invention is suitably from about 100 to 300 milligrams, and clearly, the weight of cardiac glycoside contained in each capsule will be that generally required for a unit dose, for example from 50 to 300 micrograms.

The compositions of the invention are prepared in the liquid phase so that it is impossible to obtain accurate and consistent dispersion of the active ingredient (cardiac glycoside) throughout the liquid phase of the composition. Accordingly, it is possible to insure that each dosage unit (i.e. capsule) contains the same amount (within tolerable limits) of the active ingredient.

It has also been found, that the unit dosage forms of the invention give better or more rapid availability of the active ingredient (as indicated by release tests carried out in artificial gastric juices) than do comparable tablets. Thus, it has been found not only do the capsules of the invention give a more rapid release of their contents but also they give a more complete release of their content than do the tablets which frequently release only about 50% or less of their contents. It will be appreciated, therefore, that the capsules of the invention constitute a much more releable dosage a unit than do many tablets since they can be relied upon to release substantially all of their active ingredient content within a relatively short period of time whereas this is not the case with tablets.

In order that the invention may be well understood, the following examples of formulations for 140 and 280 milligram capsules are given by way of illustration only.

EXAMPLE 1

| 140 Mg capsule containing 62.50 micrograms of digoxin | |
|---|---|
| Digoxin | 0.0625 mg. |
| Ethanol abs. | 8.5 mg. |
| Water | 1.5 mg. |
| Propylene glycol | 4.75 mg. |
| PEG 400 | 125.1875 mg. |

EXAMPLE 2

| 140 Mg capsule containing 150 micrograms of digoxin | |
| --- | --- |
| Digoxin | 0.125 mg. |
| Ethanol abs. | 8.5 mg. |
| Water | 1.5 mg. |
| Propylene glycol | 4.75 mg. |
| PEG 400 | 125.125 mg. |

EXAMPLE 3

| 280 MG capsule containing 250 micrograms of digoxin | |
| --- | --- |
| Digoxin | 0.250 mg. |
| Ethanol | 17.0 mg. |
| Water | 3.0 mg. |
| Propylene glycol | 9.5 mg. |
| PEG 400 | 250.25 mg. |

The rate of dissolution of, in 0.6% H Cl of two capsules (capsules A and B) in accordance with Example 3 and a capsule (capsule C) in accordance with Example 1 was investigated by the method of Beckett et al (The Pharmaceutical Journal, August 11, 1973, pp. 111 and 112) and the results are shown in the following table which also shows, by way of comparison, the results obtained in similar tests for commercially available tablets containing a stated 0.25 mg. of digoxin. Tablets A, B, C and D were four capsules of the same commercial tablet and tablets E.F. and G were single samples of other commercially available tablets.

TABLE

| | Percentage of Digoxin Content Dissolved | | | | | | | | | |
| --- | --- | --- | --- | --- | --- | --- | --- | --- | --- | --- |
| | Capsules | | | Tablets | | | | | | |
| Time (minutes) | A | B | C | A | B | C | D | E | F | G |
| 5 | 8 | 6 | 25 | — | — | — | — | — | — | — |
| 10 | 12 | 14 | 68 | — | — | — | — | — | — | — |
| 15 | 31 | 40 | 100 | 19 | 29 | 29 | 76 | — | — | 69 |
| 20 | — | 72 | — | — | — | — | — | — | — | — |
| 30 | 91 | 95 | — | 28 | 35 | 29 | 80 | 25 | 30 | 79 |
| 45 | — | 93 | — | — | — | — | — | — | — | — |
| 60 | — | — | — | 37 | 45 | 53 | 96 | — | — | 100 |
| 120 | — | — | — | — | — | — | — | — | — | 103 |
| 240 | — | 93 | — | — | — | — | — | — | — | — |

While in the foregoing, there has been provided a detailed description of particular embodiments of my invention, it is to be understood that all equivalents obvious to those having skill in the art are to be included within the scope of the invention, as claimed.

What I claim and desire to secure by Letters Patent is:

1. A cardiotonic dosage unit form comprising a soft elastic gelatin capsule containing about 100–300 milligrams of a liquid solution consisting essentially of (a) about 50–300 micrograms of a digitalis cardiac glycoside selected from digoxin, digitoxin, digitalin, lanatoside C., acetyl digitoxin, acetyl digoxin or methyl digoxin, (b) ethanol, (c) water, said water forming less than about 25% by weight of the total of the water and the ethanol in said solution, the weight ratio of said water and said ethanol to said digitalis cardiac glycoside being about 80:1 or higher, (d) propylene glycol, glycerine or mixtures thereof, and (e) liquid polyethylene glycol, said polyethylene glycol comprising about 80–95% by weight of said solution.

2. The cardiotonic dosage unit form of claim 1 wherein said digitalis cardiac glycoside is digoxin.

3. The cardiotonic dosage unit form of claim 1 wherein said polyethylene glycol comprises about 89% by weight of said liquid cardiotonic composition.

4. The cardiotonic dosage unit form of claim 3 wherein said ethanol forms about 6% by weight of said liquid cardiotonic composition.

* * * * *